United States Patent [19]

Chen

[11] Patent Number: 5,673,825

[45] Date of Patent: Oct. 7, 1997

[54] HOLDER FOR HOLDING A DEODORANT BOTTLE THEREIN

[75] Inventor: Cheng-Feng Chen, Taipei, Taiwan

[73] Assignee: Bobson Hygiene International Inc., Taipei Hsien, Taiwan

[21] Appl. No.: 563,939

[22] Filed: Nov. 29, 1995

[51] Int. Cl.$^6$ ................................................. G05D 7/00
[52] U.S. Cl. .................. 222/646; 222/649; 222/153.03; 222/153.09; 222/181.1; 222/325; 222/333
[58] Field of Search ................... 222/153.03, 153.09, 222/181.1, 181.3, 325, 333, 402.1, 644, 645, 646, 647, 648, 649

[56] References Cited

U.S. PATENT DOCUMENTS

| | | | |
|---|---|---|---|
| 3,540,630 | 11/1970 | Brown et al. | 222/153.03 |
| 3,726,437 | 4/1973 | Siegel | 222/648 |
| 4,402,430 | 9/1983 | Fox et al. | 222/325 X |
| 5,038,972 | 8/1991 | Muderlak et al. | 222/649 X |
| 5,480,068 | 1/1996 | Frazier et al. | 222/153.03 |

Primary Examiner—Joseph Kaufman
Attorney, Agent, or Firm—Sughrue, Mion, Zinn, Macpeak and Seas

[57] ABSTRACT

A holder includes a casing, a timer-controlled press device, a holding frame, and a locking device. The casing is adapted to keep a deodorant bottle therein and has an opening formed therethrough. The timer-controlled press unit is installed in the casing and can press a spray head of the deodorant bottle at pre-set times to spray out deodorant from the bottle so that the deodorant flows out from the casing through the opening of the casing, thereby spreading fragrance around the casing. The holding frame is mounted slidably within the casing at a normal position and is adapted to carry the bottle thereon. The frame can slide on the casing to an extended position, in which the bottle can be taken out from the frame by hand for replacement. The locking device locks releasably the frame at the normal position within the casing. The locking device can be actuated by the use of a needle-shaped tool so as to unlock the frame from the casing, thus permitting movement of the frame to the extended position.

4 Claims, 5 Drawing Sheets

HOLDER FOR HOLDING A DEODORANT BOTTLE THEREIN

BACKGROUND OF THE INVENTION

1. Field of the Invention

The invention relates to a holder, more particularly to a holder for holding a deodorant bottle therein.

2. Description of the Related Art

In order to freshen the atmosphere of a public area, such as a toilet or a meeting room, a deodorant bottle is placed in a holder, which is generally fixed on the wall of the public area.

The drawback resulting from the use of the aforesaid holder is that the bottle is usually exposed to an exterior of the holder, thereby making it easy to steal the bottle.

SUMMARY OF THE INVENTION

The main object of this invention is to provide a holder which is adapted to hold a deodorant bottle therein in such a manner that the deodorant bottle cannot be easily taken away, and which permits the bottle to be replaced with a new one by using a needle-shaped tool.

Accordingly, the holder of this invention includes a casing, a timer-controlled press device, a holding frame, and a locking device. The casing is adapted to keep a deodorant bottle therein and has an opening formed therethrough. The timer-controlled press device is installed in the casing and can press a spray head of the deodorant bottle at pre-set times to spray out deodorant from the bottle so that the deodorant flows out from the casing through the opening of the casing, thereby spreading fragrance around the casing. The holding frame is mounted slidably within the casing at a normal position and is adapted to carry the bottle thereon. The frame can slide on the casing to an extended position, in which the bottle can be taken out from the frame by hand for replacement. The locking device locks releasably the frame at the normal position within the casing. The locking device can be actuated by means of a needle-shaped tool so as to unlock the frame from the casing, thus permitting movement of the frame to the extended position.

BRIEF DESCRIPTION OF THE DRAWINGS

Other features and advantages of this invention will become more apparent in the following detailed description of the preferred embodiment with reference to the accompanying drawings, in which.

DETAILED DESCRIPTION OF THE PREFERRED EMBODIMENT

Figure 1:
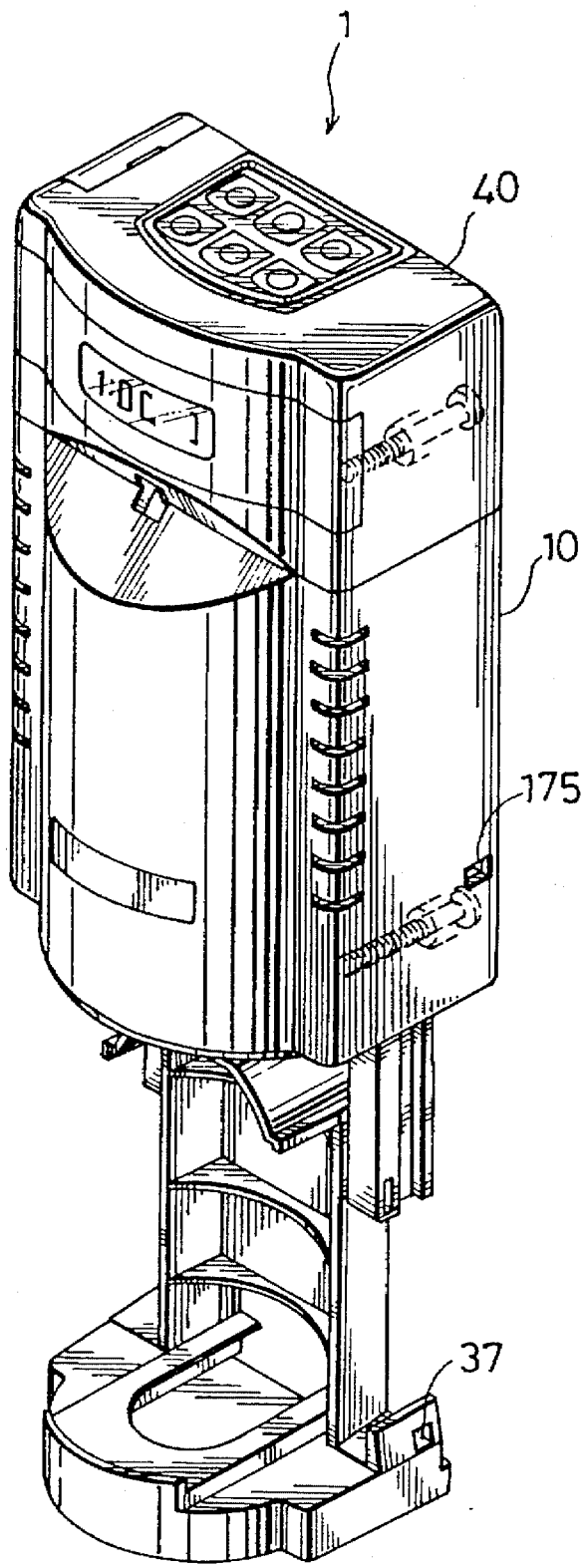
FIG. 1 is a perspective view showing a holder of this invention, in which a holding frame is extended outward from the holder so as to permit a deodorant bottle to be placed thereon.
Figure 2:
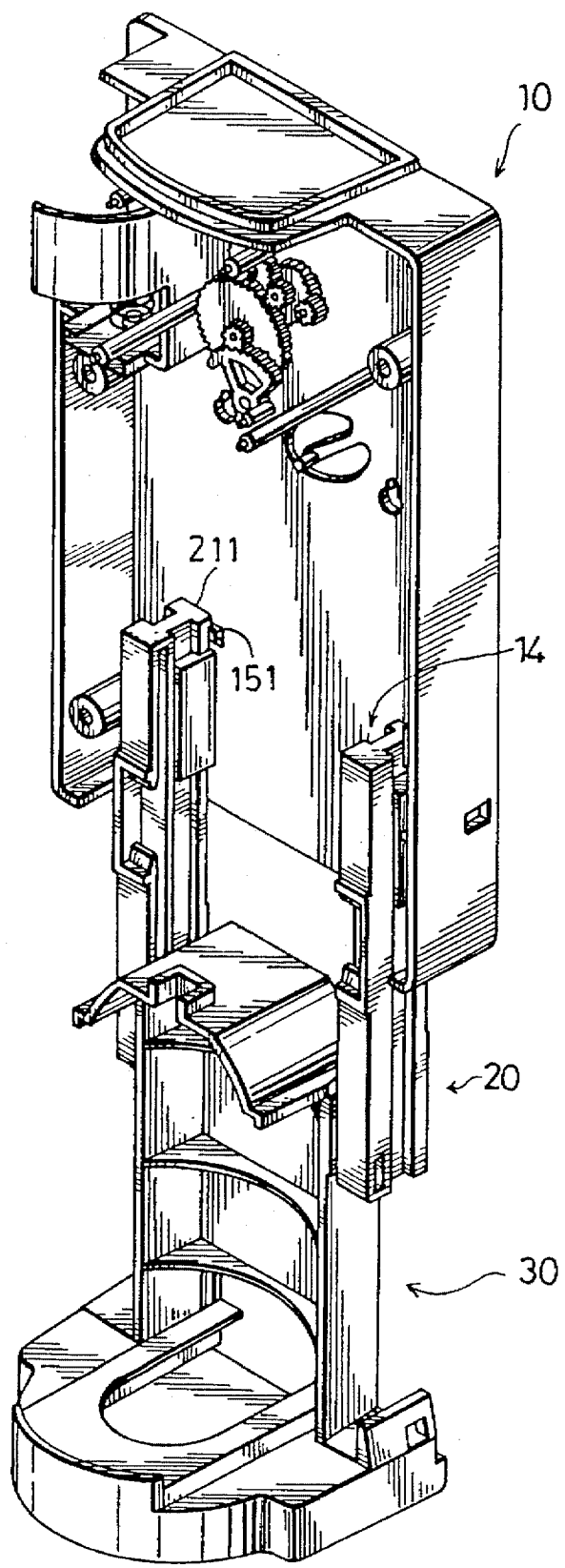
FIG. 2 is a view similar to FIG. 1, except that a cover member is removed from the holder of this invention.

Referring to FIGS. 1 and 2, a holder of this invention includes a casing 1 formed by a vertical mounting plate 10 and a rectangular cover member 40 secured on the plate 10 in a conventional manner, a timer-controlled press device, a pair of slide-holding units 14, a pair of elongated slides 20, a holding frame 30, and a locking device.

Figure 3:
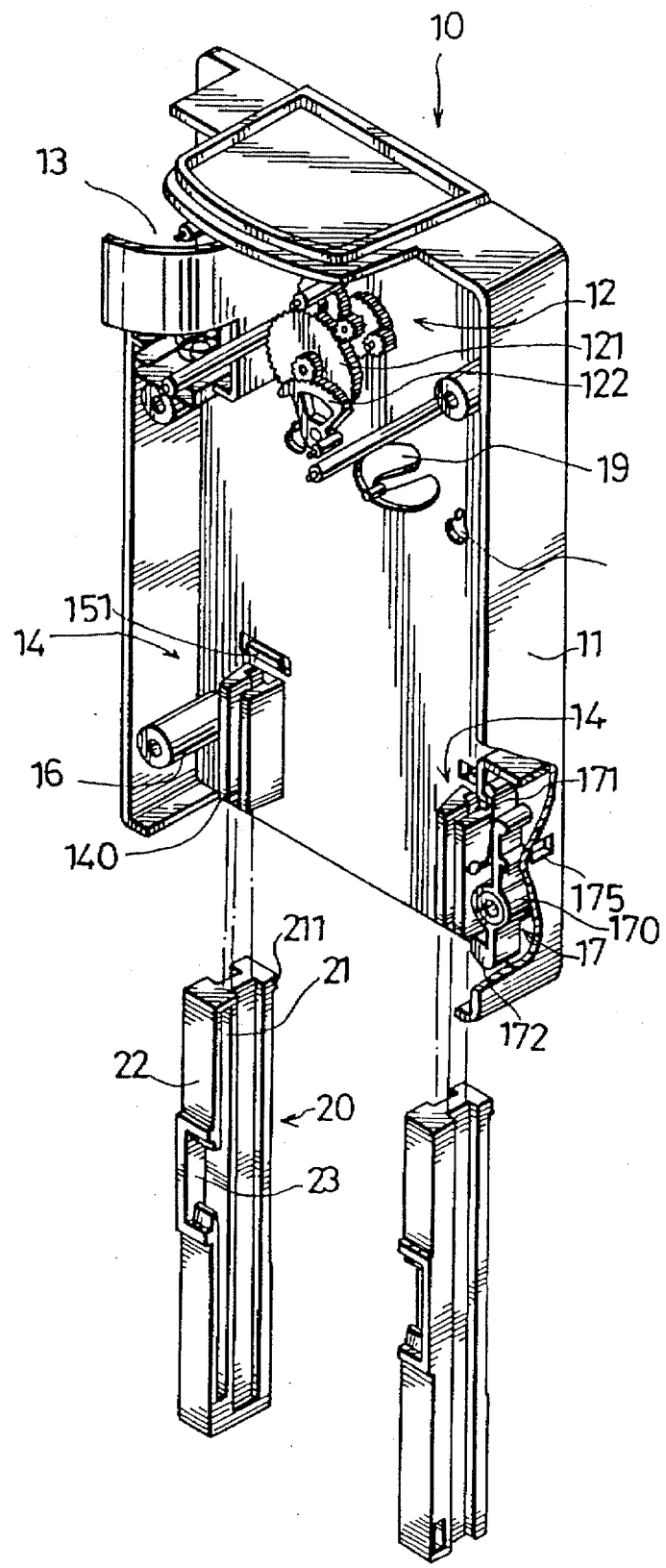
FIG. 3 illustrates how two elongated slides are mounted in two slide-holding units that are fixed on the mounting plate of the holder shown in FIG. 1.

As illustrated in FIG. 3, the slide-holding units 14 are fixed on a lower portion of the vertical mounting plate 10. Each of the slide-holding units 14 is formed with an engaging channel 140 therethrough which has a T-shaped cross section. Each of the slides 20 has a generally I-shaped cross section and is received slidably in the channel 140 of the corresponding slide-holding unit 14. The slide 20 further has a lengthwise extending engaging slot 21 formed in a side surface thereof, and an access 23 formed through the external planar wall 22 thereof and in communication with the slot 21. The slides 20 are slidable downwardly on the mounting plate 10 to a lower position shown in FIGS. 1 and 2, wherein the lower portions of the slides 20 are exposed to an exterior of the casing 1. At this condition, as best shown in FIG. 2, the stubs 151 project outwardly from the mounting plate 10 to abut against the stops 211 of the slides 20 so as to prevent disengagement of the slides 20 from the plate 10.

Figure 4:
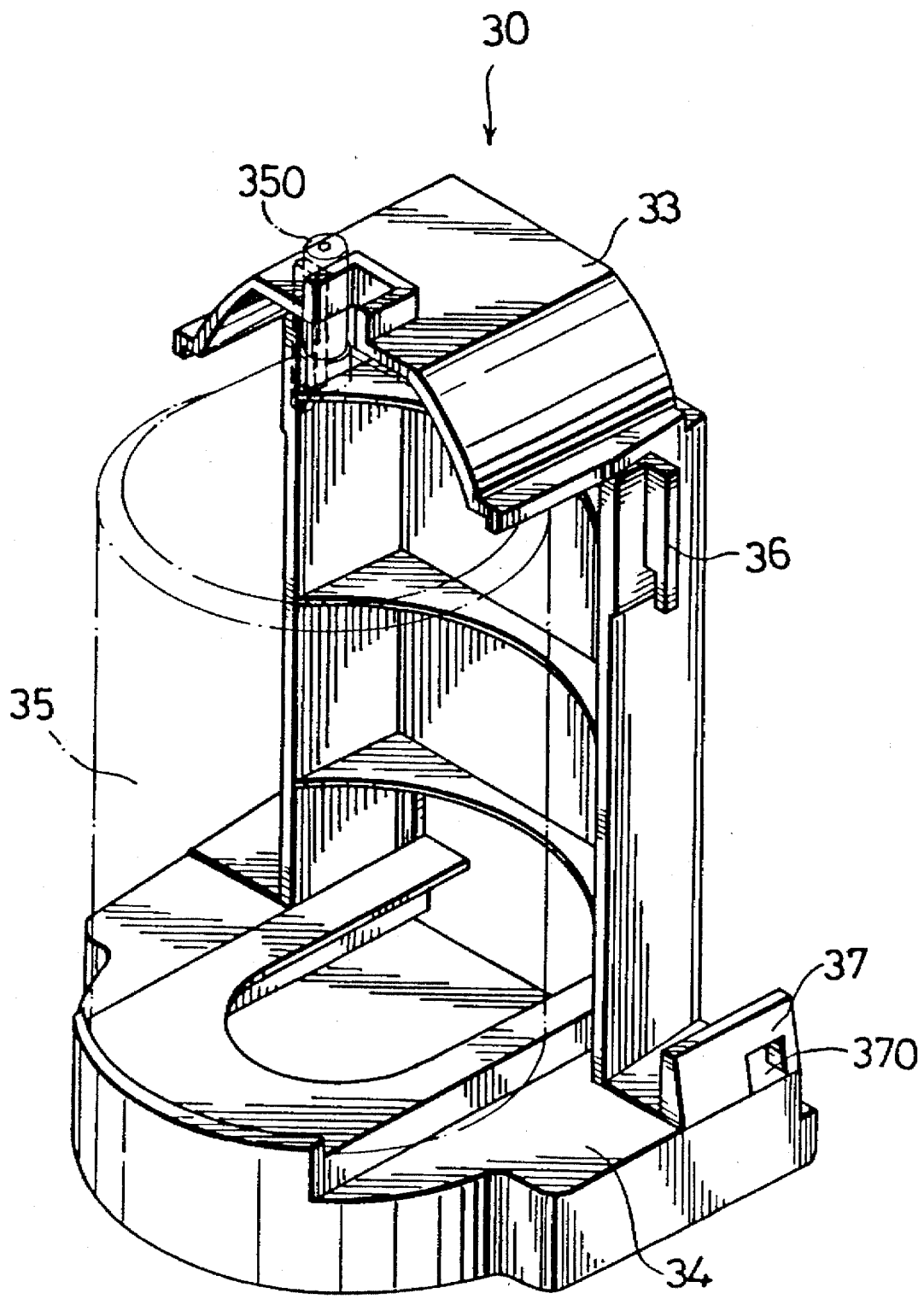
FIG. 4 illustrates how a deodorant bottle is placed on the holding frame of the holder of this invention.
Figure 5:
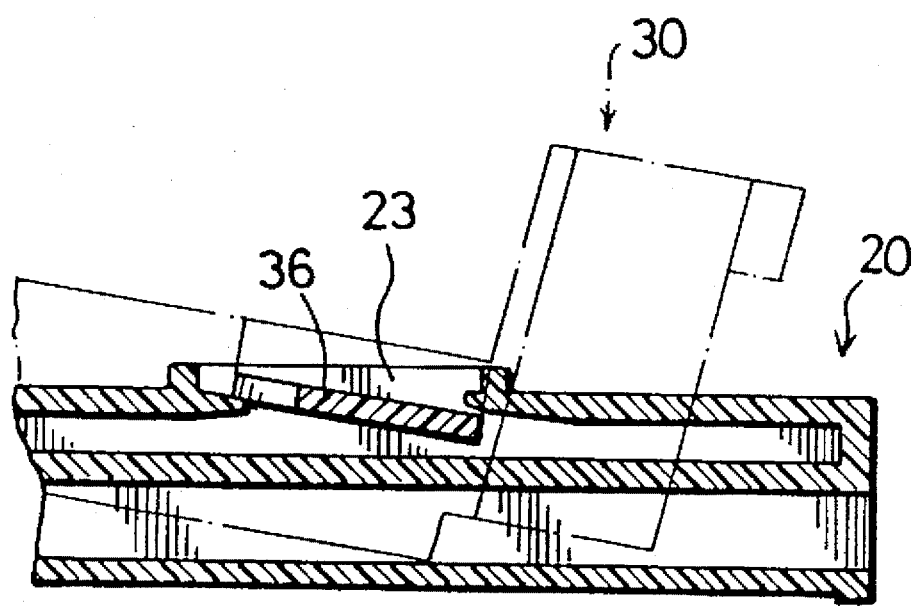
FIG. 5 shows the connection between the holding frame and the slides of the holder according to this invention.

Referring to FIGS. 3 and 4, the holding frame 30 is a unitary piece and has a bottom portion 34 and an upper portion 33 between which a deodorant bottle 35 can be accommodated. The lateral lugs 36 of the holding frame 30 are respectively inserted into the slots 21 of the slides 20 through the accesses 23 (see FIG. 5) of the slides 20. Thus, when in an extended position, the frame 30 is located under the slides 20, as illustrated in FIG. 2, for convenience during replacement of the bottle 35.

The timer-controlled press device of a known art is installed on the upper portion of the mounting plate 10 thereof and includes a battery accommodating space 13, a motor (not shown), a speed reduction gear unit 12 connected to the motor and provided with a gear disk 121 and an actuator 122 operably connected with the disk 121, and a timer (not shown). The actuator 122 is arranged to press the spray head 350 of the deodorant bottle 35 at pre-set times to spray out deodorant from the bottle 35 so that the deodorant flows out from the casing 1 through the opening 19 of the mounting plate 10. Thus, fragrance is spread around the casing 1.

The locking device includes a crank member 17 having a middle portion mounted pivotally on the mounting plate 10 near the right side slide-holding unit 14. The crank member 17 is a one-piece plastic member and further has an actuator crank arm 170 at the upper portion thereof that has two curved integral push bar sections 171, and a locking crank arm formed with a tongue 172. The distal ends of the bar sections 171 of the crank member 17 abut against a portion of the mounting plate 10 so as to bias the tongue 172 to engage the groove 370 (see FIG. 4) formed in the planar side surface 37 of the frame 30 Thus, the frame 30 is locked at the normal position within the casing 1 against movement to the extended position.

When it is desired to replace the deodorant bottle, a needle-shaped tool (not shown) can be inserted via the tool opening 175 formed through a side wall 11 of the casing 1 in order to impel the actuator crank arm 170 of the crank member 17 away from the side wall 11 of the casing 1, thereby disengaging the tongue 172 from the groove 370 of the frame 30. Thus, the frame 30 extends automatically by virtue of gravity to the extended position.

Note that the tongue 172 of the locking crank arm has a sliding surface at a distal end portion thereof which is inclined relative to the planar side wall 37 of the frame 30 so as to assist in movement of the frame 30 from the extended position to the normal position.

With this invention thus explained, it is obvious to those skilled in the art that various modifications and variations can be made without departing from the scope and spirit of this invention. It is therefore intended that the invention be limited only as in the appended claims.

I claim:

1. A holder adapted to hold therein a deodorant bottle which has a spray head, said holder comprising:

a casing having an opening formed therethrough;

a timer-controlled press device installed in said casing and capable of pressing the spray head of said deodorant bottle at pre-set times to spray out deodorant from said bottle so that the deodorant flows out from said casing through said opening, thereby spreading fragrance around said casing;

a holding frame mounted slidably at a normal position within said casing, said holding frame being adapted to carry the bottle thereon and being slidable on said casing to an extended position, in which said bottle can be taken out from said frame by hand for replacement; and a locking device for locking releasably said frame at said normal position within said casing, said locking device being capable of being externally actuated by means of a tool so as to unlock said frame from said casing, thus permitting movement of said frame to said extended position.

2. The holder as defined in claim 1, wherein said frame has a planar side surface with a groove formed therein, said locking device including a crank member mounted pivotally in said casing, said casing having a side wall formed with a tool opening, said crank member having a locking crank arm with a tongue engaged within said groove of said frame so as to lock said frame against movement to said extended position, and an actuator crank arm biased toward said side wall so as to engage said tongue of said locking crank arm within said groove of said frame, said actuator crank arm being positioned in said casing so that the tool can be passed through said tool opening of said casing in order to impel said actuator crank arm of said crank member away from said side wall of said casing, thereby disengaging said tongue of said crank member from said groove of said frame and permitting movement of said frame to said extended position, said tongue having a sliding surface at a distal end portion thereof, said sliding surface being inclined relative to said planar side wall of said frame so as to assist in movement of said frame from said extended position to said normal position.

3. A holder as claimed in claim 2, wherein said actuator crank arm of said crank member is made of one-piece plastic member and has two curved integral push bar sections with distal ends that abut against a portion of said casing so as to bias said tongue to engage said groove.

4. A holder as claimed in claim 3, wherein said casing includes a vertical mounting plate having an opposed pair of slide-holding units fixed on said mounting plate, and a pair of elongated slides attached respectively and slidably in said slide-holding units in such a manner that said slides are slidable downwardly on said mounting plate to a lower position, wherein lower portions of said slides are exposed to an exterior of said casing, each of said slides having a lengthwise extending engaging slot formed therein, said holding frame being a unitary piece and having an opposed pair of lateral lugs slidably engaging said slots of said slides, said frame being located under said casing when in said extended position for convenience during replacement of said bottle, whereby, when the tool is pressed on said actuator crank arm so as to disengage said tongue from said groove, said frame descends to said extended position by virtue of gravity.

* * * * *